(12) United States Patent
Barnes (10) Patent No.: US 9,192,711 B2
(45) Date of Patent: Nov. 24, 2015

(54) MODULAR INFUSION SYSTEM

(75) Inventor: Erik Barnes, Solana Beach, CA (US)

(73) Assignee: CareFusion 303, Inc., San Diego, CA (US)

( * ) Notice: Subject to any disclaimer, the term of this patent is extended or adjusted under 35 U.S.C. 154(b) by 1050 days.

(21) Appl. No.: 12/890,432

(22) Filed: Sep. 24, 2010

(65) Prior Publication Data

US 2012/0078218 A1   Mar. 29, 2012

(51) Int. Cl.
*A61M 1/00* (2006.01)
*A61M 5/14* (2006.01)
*A61M 5/142* (2006.01)

(52) U.S. Cl.
CPC .............. *A61M 5/1413* (2013.01); *A61M 5/142* (2013.01); *A61M 5/14228* (2013.01); *A61M 5/14232* (2013.01); *A61M 5/14244* (2013.01); *A61M 2205/3351* (2013.01); *A61M 2205/3355* (2013.01); *A61M 2205/3553* (2013.01); *A61M 2205/3584* (2013.01); *A61M 2205/8206* (2013.01); *A61M 2209/086* (2013.01)

(58) Field of Classification Search
CPC .......... A61M 5/1413; A61M 5/14228; A61M 5/142; A61M 2205/3561; A61M 2005/14208; A61M 2205/3584; A61M 2005/3126; A61M 2005/31588; A61M 2205/8256; A61M 2209/086; A61M 5/14244; A61M 5/31533; A61M 5/143

USPC ........................................... 604/67, 131, 151
See application file for complete search history.

(56) References Cited

U.S. PATENT DOCUMENTS

| | | | |
|---|---|---|---|
| 4,898,578 A | | 2/1990 | Rubalcaba, Jr. |
| 5,782,805 A | * | 7/1998 | Meinzer et al. ............... 604/131 |
| 5,904,668 A | * | 5/1999 | Hyman et al. ................ 604/131 |
| 7,713,240 B2 | | 5/2010 | Istoc et al. |
| 2004/0171985 A1 | * | 9/2004 | Schubert et al. ........... 604/93.01 |
| 2006/0122577 A1 | * | 6/2006 | Poulsen et al. ............. 604/890.1 |
| 2008/0045904 A1 | | 2/2008 | Estes et al. |
| 2009/0177142 A1 | * | 7/2009 | Blomquist et al. .............. 604/66 |
| 2009/0275886 A1 | * | 11/2009 | Blomquist et al. .............. 604/66 |

* cited by examiner

*Primary Examiner* — Kami A Bosworth
*Assistant Examiner* — Brandy S Lee
(74) *Attorney, Agent, or Firm* — McDermott Will & Emery LLP (57) ABSTRACT

A pump is disclosed that comprises a primary control unit comprising a first processor and one or more modular pumping units removably docked to the primary control unit. Each modular pumping unit comprises a pumping mechanism and a second processor configured to control the pumping mechanism and communicate with the first processor. The modular pumping unit is configured to manipulate a portion of a fluid delivery set to pump a fluid. The first processor and the second processor are configured to exchange one or more operating parameters when the modular pumping unit is docked to the primary control unit. The modular pumping unit is configured to pump the fluid after being undocked.

29 Claims, 7 Drawing Sheets

MODULAR INFUSION SYSTEM

BACKGROUND

1. Field

The present disclosure generally relates to systems and methods of delivering medical fluid to patients, and, in particular, relates to infusion pumps.

2. Description of the Related Art

Infusion pumps have become commonplace within the healthcare world as a way to precisely administer intravenous (IV) fluids. Use of a pump in place of an elevated fluid container with a simple roller clamp to control the flow of the IV fluid allows more accurate and consistent control of the rate of delivery of the fluid to the patient.

Figure 1:
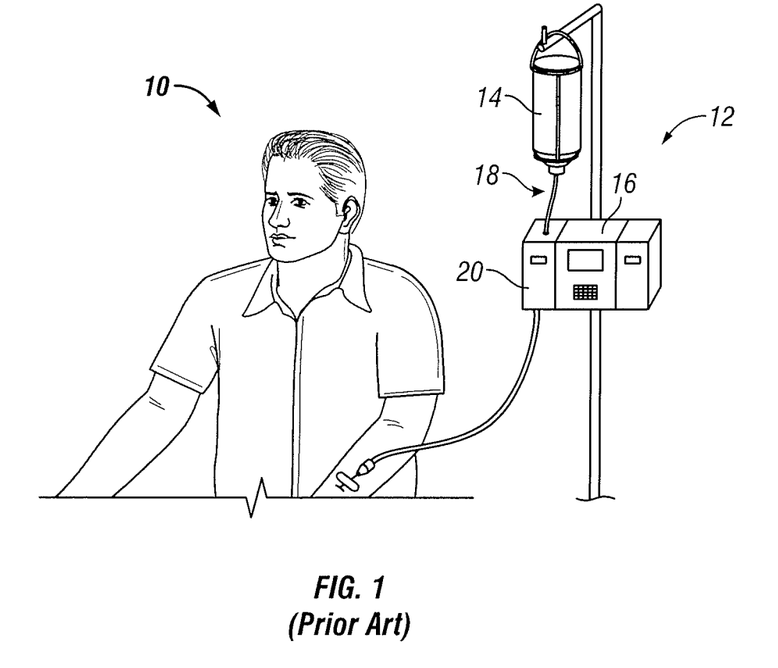
FIG. 1 depicts a patient receiving an infusion of a medical fluid using an IV pump in accordance with the prior art.

The assembly of tubing, valves, fittings, and needles that connect the fluid container to the patient may be referred to as an "IV set." IV sets are typically disposable to reduce the risk of infection and contamination. When used with an infusion pump, the IV set includes a segment intended to be manipulated by the pump to cause the fluid to flow at a controlled rate. For a peristaltic type of pump, this segment may be as simple as a length of tubing that is fitted into the pumping compartment. A patient 10 receiving an infusion of medical fluid from source of medical fluid 14 delivered by a typical IV pump system 12 using an IV set 18 is shown in FIG. 1.

Many IV pumps are large and heavy enough that they are mounted on a rolling stand that may be positioned next to the bed or rolled by the patient as they walk around the room or hospital. Walking while pushing one of these rolling stands is sometimes awkward for the patient, as the patient may be weak or have impaired balance as a result of injury or surgery.

Some IV pumps are modular, in that there is a main unit that contains the control system to which can be attached additional modules that may have one or more of a variety of functions. FIG. 1 illustrates an example modular IV pump 12 wherein the control unit 16 contains the processor, memory, and user interface with two pumping modules 20 attached, one module 20 on each side.

SUMMARY

For some or all of the reasons listed above, it is advantageous to provide a modular IV pump wherein modules may be added and removed individually without impact on the operation of other modules attached to the IV pump. Once removed, it is advantageous for these modules to be independently operable. Modules that can continue to operate independent of the primary control unit provide increased mobility and convenience to the patient.

In certain embodiments, a pump is disclosed that comprises a primary control unit comprising a first processor and one or more modular pumping units removably docked to the primary control unit. Each modular pumping unit comprises a pumping mechanism and a second processor configured to control the pumping mechanism and communicate with the first processor. The modular pumping unit is configured to manipulate a portion of a fluid delivery set to pump a fluid. The first processor is configured to program the second processor with a set of one or more operating parameters when the modular pumping unit is docked to the primary control unit. The modular pumping unit is configured to pump the fluid after being undocked.

In certain embodiments, a method of delivering fluid is disclosed, the method comprising the steps of coupling a modular pumping unit to a primary control unit, coupling a cassette of a delivery set to the modular pumping unit, coupling the delivery set to a source of fluid and to a receiver such that manipulation of the cassette will transfer fluid from the source to the receiver, configuring the modular pumping unit to manipulate the cassette wherein the configuring is accomplished through the primary control unit, starting the modular pumping unit wherein the starting is accomplished through the primary control unit, and removing the modular pumping unit from the primary control unit wherein the modular pumping unit continues to manipulate the cassette.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

IV pumps are frequently large and heavy, making it difficult for a patient to move around the hospital while receiving a fluid via an infusion pump. In addition, at least some current modular IV pumps have modules sequentially attached such that the inside modules cannot be removed from the system without first removing modules that are connected to the outside of that module. These inside modules are referred to as "trapped" modules. This limits the availability of the inside modules for use on other systems even when they are not being used in the system in which they are installed.

The disclosed modular infusion system presents a number of improvements over existing IV pumps including avoidance of trapped modules, and provides small pumping modules that are operative after being removed from the primary control unit. Having a small, easily removed pumping module enables a patient to disconnect the module and move about carrying only the small module and the fluid container. The ability to remove any module from the system without impact to the operation of the other modules in the system enables easy reassignment of modules within a system.

In the following detailed description, numerous specific details are set forth to provide a full understanding of the present disclosure. It will be apparent, however, to one ordinarily skilled in the art that embodiments of the present disclosure may be practiced without some of the specific details.

In other instances, well-known structures and techniques have not been shown in detail so as not to obscure the disclosure.

While the following discussion is directed to the administration of medical fluid to a patient by a nurse using an IV pump, the disclosed methods and configurations may be used for other medical and non-medical applications and may be used by other individuals, for example a patient self-administering a medical fluid at home.

FIG. 1 depicts a patient 10 receiving an infusion of a medical fluid using an IV pump 12. A fluid container 14 is hung at or above the patient's head and connected via an IV set 18 to an IV pump 12 and then to the patient 10. In this example, the IV pump 12 includes a control module 16 and a pumping module 20.

Figure 2:
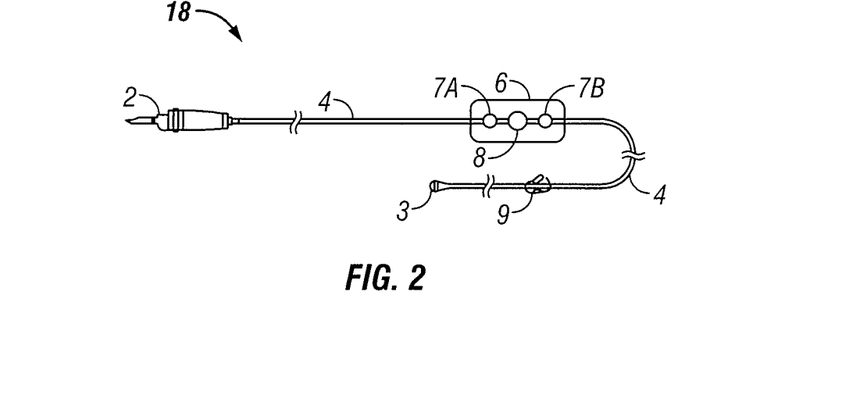
FIG. 2 depicts an example IV set.

FIG. 2 depicts an example IV set 18. This example IV set 18 includes a bag spike 2 that is configured to connect to a fluid source such as fluid container 14 of FIG. 1. The bag spike 2 is connected through tubing 4 to a cassette 6 which is then connected through additional tubing 4 to a fitting 3. In this example, fitting 3 is a needleless Luer connector suitable for connection to any patient infusion device (not shown) such as an intravenous needle. Cassette 6 includes a pumping element 8 and two pressure sensing elements 7A and 7B that are connected to the fluid lines upstream and downstream, respectively, of pumping element 8. An IV pump 12 can monitor the pressure in pressure sensing element 7B to detect occlusions of the line 4 between the cassette 6 and the patient 10, and likewise monitor the pressure in pressure sensing element 7A to detect a blockage of the line between the fluid container 14 and the IV pump 12. IV set 18 also includes a clamp 9 that can be closed to stop flow through the tubing 4.

Figure 3:
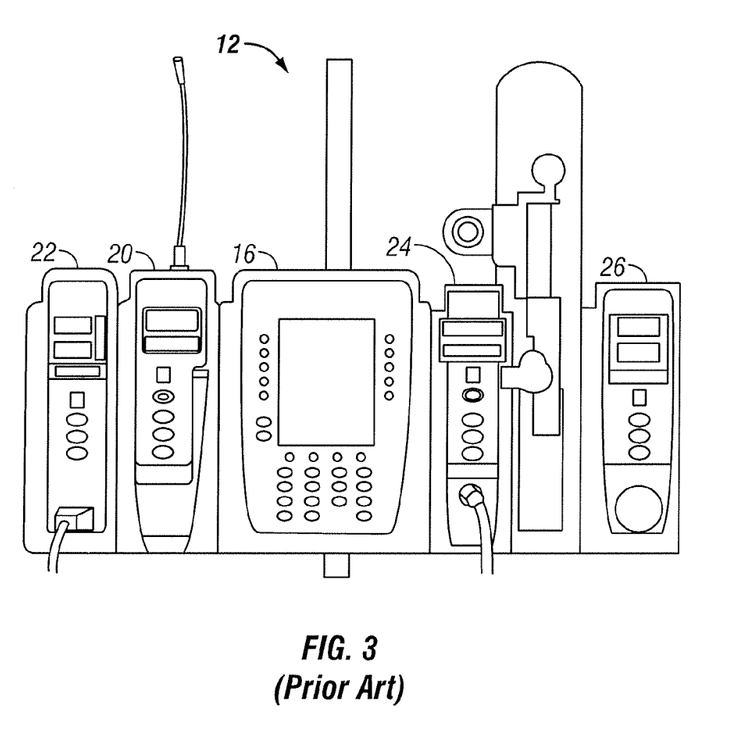
FIG. 3 depicts an example configuration of an Alaris System IV pump in accordance with the prior art.

FIG. 3 depicts an example configuration of an Alaris® System IV pump 12 manufactured by CareFusion of San Diego, Calif., USA. The pump 12 has a central control unit 16 and four auxiliary modules including a $SpO_2$ monitor 22, a pumping module 20, a patient-controlled analgesia (PCA) module 24, and a $EtCO_2$ monitor 26. It can be seen that, in this example, it is not possible to remove an inside or "trapped" module, such as module 20 or module 24, without disconnecting the respective outside module 22 or 26. In addition, the pumping modules 20, 22, 24, and 26 are not functional by themselves and can only be used when attached to the central control unit 16. The entire IV pump 12 must be taken along whenever the patient 10 leaves the patient's bed.

Figure 4:
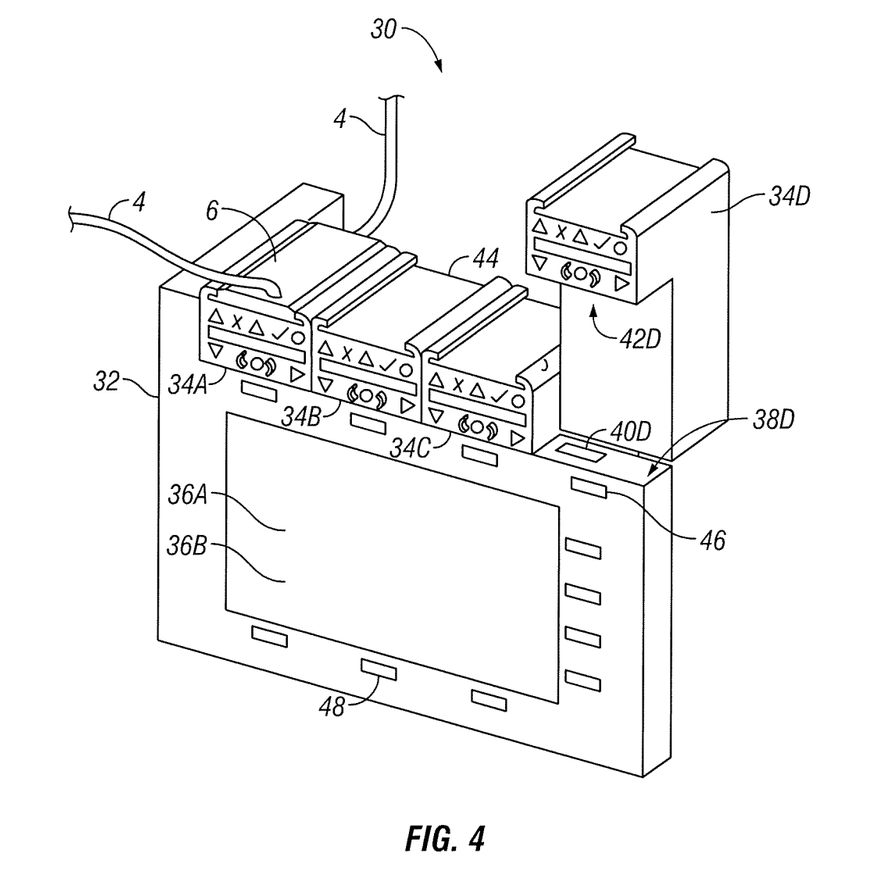
FIG. 4 discloses an exemplary embodiment of a modular infusion system according to certain aspects of the present disclosure.

FIG. 4 discloses an exemplary embodiment of a modular infusion system 30 according to certain aspects of the present disclosure. The modular infusion system 30 includes a primary control unit 32 and, in this example, four modular pumping units 34 that have been designated as units 34A, 34B, 34C, and 34D to differentiate among them in this description. Modular pumping units 34A-34C are shown as docked while unit 34D is shown as separated (undocked) from primary control unit 32. The docking location 38D is visible in front of modular pumping unit 34D, including the docking connector 40D. Modular pumping unit 34D includes a docking connector 42D (not visible in this view) that will mate with connector 40D when modular pumping unit 34D is docked with primary control unit 32. A cassette 6 from an IV set 18 such as shown in FIG. 3 is shown installed on modular pumping unit 34A along with portions of the tubing 4 that are attached to the cassette 6. An empty cassette attachment area 44 is visible on the top of modular pumping unit 34B into which a cassette may be slid. Other attachment configuration may be employed.

In the arrangement of FIG. 4, the primary control unit 32 includes channel selection buttons 46 for each of the docking locations 38, wherein information related to the selected module pumping unit 34 is displayed on the display screen 36A. The primary control unit 32 also includes a display screen 36A having a touchscreen overlay 36B (not separately visible) and a plurality of actuator buttons 48 that can be used to operate primary control unit 32. In addition, a "soft" keypad (not shown) may be displayed on display screen 36A and the touchscreen overlay 36B will detect a nurse or other user pressing the keys of the soft keypad.

Figure 5:
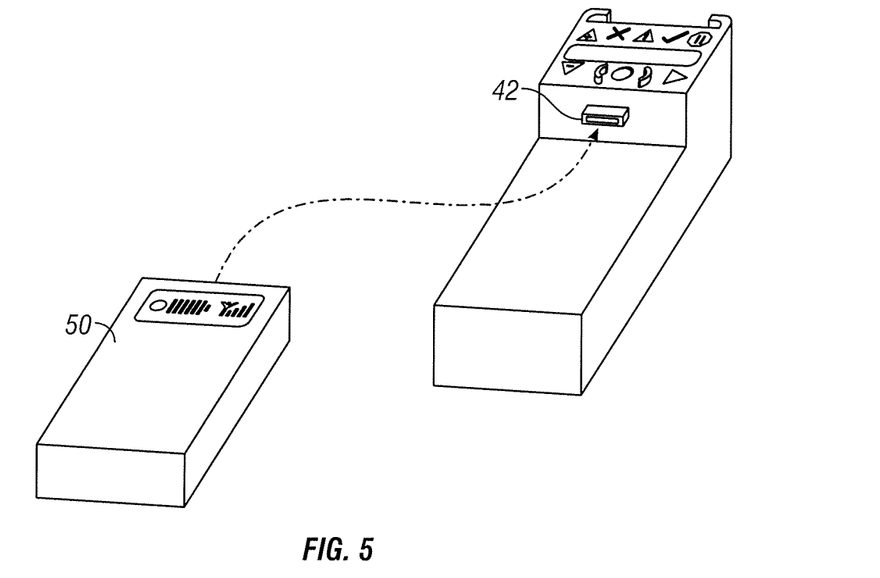
FIG. 5 depicts a single modular pumping unit and an associated battery pack to form a unit according to certain aspects of the present disclosure.

FIG. 5 depicts a single modular pumping unit 34 coupled to a battery pack 50 to form a unit according to certain aspects of the present disclosure. Docking connector 42 is visible in this view of modular pumping unit 34. The battery pack 50 includes a connector (not visible) that will mate with docking connector 42 when the battery pack 50 is inserted as indicated by the arrow and will provide power and other functions, discussed in detail below, to the modular pumping unit 34.

Figure 6:
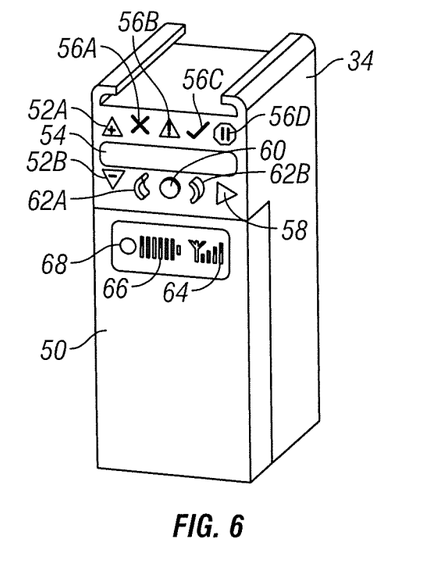
FIG. 6 discloses a combined modular pumping unit coupled to a battery pack according to certain aspects of the present disclosure.

FIG. 6 discloses a combined modular pumping unit 34 and battery pack 50 according to certain aspects of the present disclosure. This exemplary modular pumping unit 34 includes several simple input elements 52A, 52B, 56D, and 58 and visual indicators 54, 56A, 56B, 56C, and 56D (56D is both a visual indicator and an input element). In this example, buttons 52A and 52B increase and decrease, respectively, the flow rate of modular pumping unit 34. Button 58, in this example, starts the infusion while button 56D pauses/stops the infusion. Button 60 releases the modular pumping unit 34 from the primary control unit 32 when docked and releases the battery pack 50 when the modular pumping unit 34 is operating independently. Button 60 is protected by protrusions 62A and 62B that reduce the chance of accidental activation of button 60 by pressing it against a hard surface. Of the visual indicators in this exemplary configuration, indicator 56A is a red "X" that indicates, when lit, that the modular pumping unit 34 is experiencing an error condition. Indicator 56B is a yellow warning triangle that, when lit, indicates that there is a non-serious issue that should be examined by a nurse or other caregiver. Indicator 56C is a green check mark that, when lit, indicates that modular pumping unit 34 is currently pumping and that all functions are operating correctly. Indicator 56D is a red stop sign that, when lit, indicates that there is a problem that needs immediate attention and that the pump has been stopped.

The battery pack 50, in this example, has two visual indicators 64 and 66 and an input device 68. Visual indicator 64 is a multi-element light emitting diode (LED) with a series of bars of increasing height wherein the bars are sequentially illuminated from shortest to tallest to indicate the strength of the wireless signal sensed by the communication module 98 (not shown in FIG. 6) that is part of the battery pack 50. Visual indicator 66 is a multi-element LED with a series of bars of equal height wherein the bars are sequentially illuminated from left to right to indicate the amount of energy remaining in the battery pack 50. Button 68 initiates a battery test mode wherein the visual indicator 66 becomes active for a few seconds and then visual indicator 66 turns off to conserve power.

In certain embodiments, modular pumping unit 34 is used as a stand-alone IV pump to deliver medical fluid to a patient 10 without the use of a primary control unit 32. For example, it may be desirable to provide a basic infusion pump to a patient 10 so that they may receive medical fluid by infusion at home or during their normal activities. The controls of the modular pumping unit 34 shown in FIG. 6 are sufficient for a patient to manually control the infusion flow rate. The modular pumping unit 34 is small enough that it could be easily carried in a purse or hooked on a belt such that the patient 10 is able to move around with minimal inconvenience while receiving an infusion of medical fluid. In certain embodiments wherein the modular pumping unit 34 or the battery pack 50 comprise a wireless communication module 98, the modular pumping unit 34 is programmed over the wireless link from a monitoring/control application running on the primary control unit 32 or other processor.

Figure 7:
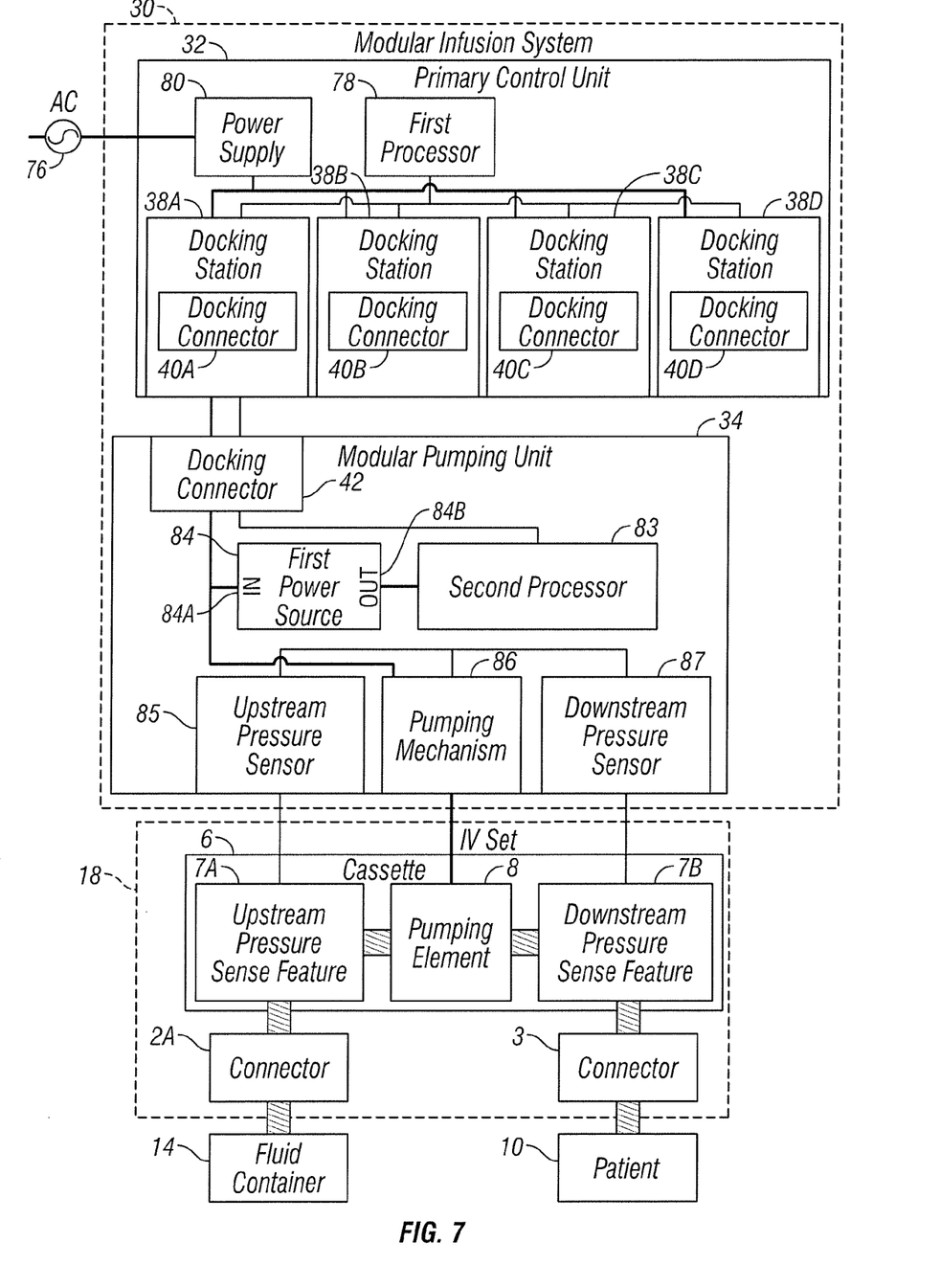
FIG. 7 is a block diagram of an exemplary configuration of a modular infusion system according to certain aspects of the present disclosure.

FIG. 7 is a block diagram of an exemplary configuration of a modular infusion system 30 according to certain aspects of the present disclosure. Modular infusion system 30, in this example, is shown with a primary control unit 32 and a single modular pumping unit 34. The primary control unit 32, in this example, includes four docking stations 38, designated 38A-38D to differentiate them, each having a docking connector 40, designated as 40A-40D herein. The primary control unit 32 also includes a first processor 78 that is coupled to the docking connectors 40. In some embodiments, there are multiple processors that handle portions of the function of first processor 78. A power supply 80 draws power from an external source 76 and is also coupled to the docking connectors 40 through the docking stations 38 to provide power to the modular pumping units 34 when docked, wherein power connections are shown in FIG. 7 by the thicker lines.

Modular pumping unit 34 includes a docking connector 42 that is, in this example wherein the modular pumping unit 34 is docked to docking station 38A, mated to the docking connector 40A, a second processor 83, a first power source 84, a pumping mechanism 86, and, in this example, an upstream pressure sensor 85 and a downstream pressure sensor 87. The second processor 83 communicates through docking connectors 42 and 40 with the first processor 78. The second processor 83 is also coupled to the pressure sensors 85 and 87 as well as pumping mechanism 86, wherein the second processor 83 is configured to receive signals from the pressure sensors 85 and 87 and to control the operation of pumping mechanism 86. The output 84B of first power source 84, in this embodiment, is coupled only to the second processor 83. The first power source 84 draws power through input 84A from the power supply 80 through the docking connectors 40A, in this example, and 42 to charge the first power source 84 as well as supply power at the output 84B. In certain embodiments, the second processor 83 enters a standby mode to conserve battery power when modular pumping unit 34 is undocked from primary control unit 32 and remains in the standby mode until a battery pack 50 is attached. The output 84B of the first power source 84, in these embodiments, provides only standby power to the second processor 83 and can be a small battery such as used in digital watches. In certain other embodiments, the output 84B of the first power source 84 is coupled to both the second processor 83 and the pumping mechanism 86 (this connection not shown) and the modular pumping unit 34 will continue to pump fluid after being undocked from the primary control unit 32, drawing power from the output 84B of the first power source 84.

IV set 18 is not part of the modular infusion system 30 and is shown to provide further explanation of the function of the elements of modular pumping unit 34. Similar to the IV set 18 presented in FIG. 2, this exemplary IV set 18 includes a connector 2A, a cassette 6 that includes an upstream pressure sense feature 7A, a pumping element 8, and a downstream pressure sense feature 7B. Connector 2A is coupled through upstream pressure sense feature 7A to pumping element 8 and, likewise, connector 3 is coupled through downstream pressure sense feature 7B to pumping element 8. Connector 2A is also coupled to a fluid container 14, such as an IV bag, and connector 3 is coupled to a patient 10. In certain embodiments, connector 2A is a bag spike 2 as shown in FIG. 2. In certain other embodiments, connector 2A is configured to mate with a syringe and fluid container 14 is a vented or non-vented syringe. In embodiments where fluid container 14 is a non-vented syringe, pumping element 8 is a positive displacement pumping element comprising at least one positive displacement pumping chamber. The positive displacement pumping element is configured to create a partial vacuum at connector 2A, wherein the partial vacuum is sufficient to draw fluid from a non-vented syringe. In certain embodiments, the positive displacement pumping element comprises a plurality of positive displacement pumping chambers.

In use, the cassette 6 is installed in the cassette attachment area 44 of modular pumping unit 34 wherein the pumping element 8 is positioned such that it can be manipulated by pumping mechanism 86. Similarly, the upstream and downstream sensing features 7A and 7B are positioned such that the upstream and downstream pressure sensors 85 and 87 can sense the pressure in the respective sensing feature 7A and 7B. When operating, the pumping mechanism 86 will manipulate the pumping element 8 thereby causing fluid to be drawn from fluid container 14 and delivered to the patient 10. In certain embodiments, the pumping mechanism 86 runs in reverse for a period of time and draws fluid from the patient, for example, to obtain a blood sample.

In a non-medical embodiment, the IV set 18 is replaced by a similar delivery set (not shown) that is configured to couple to a fluid source (not shown) in place of the fluid container 14 and to a receiver (not shown) in place of the patient 10.

Figure 8:
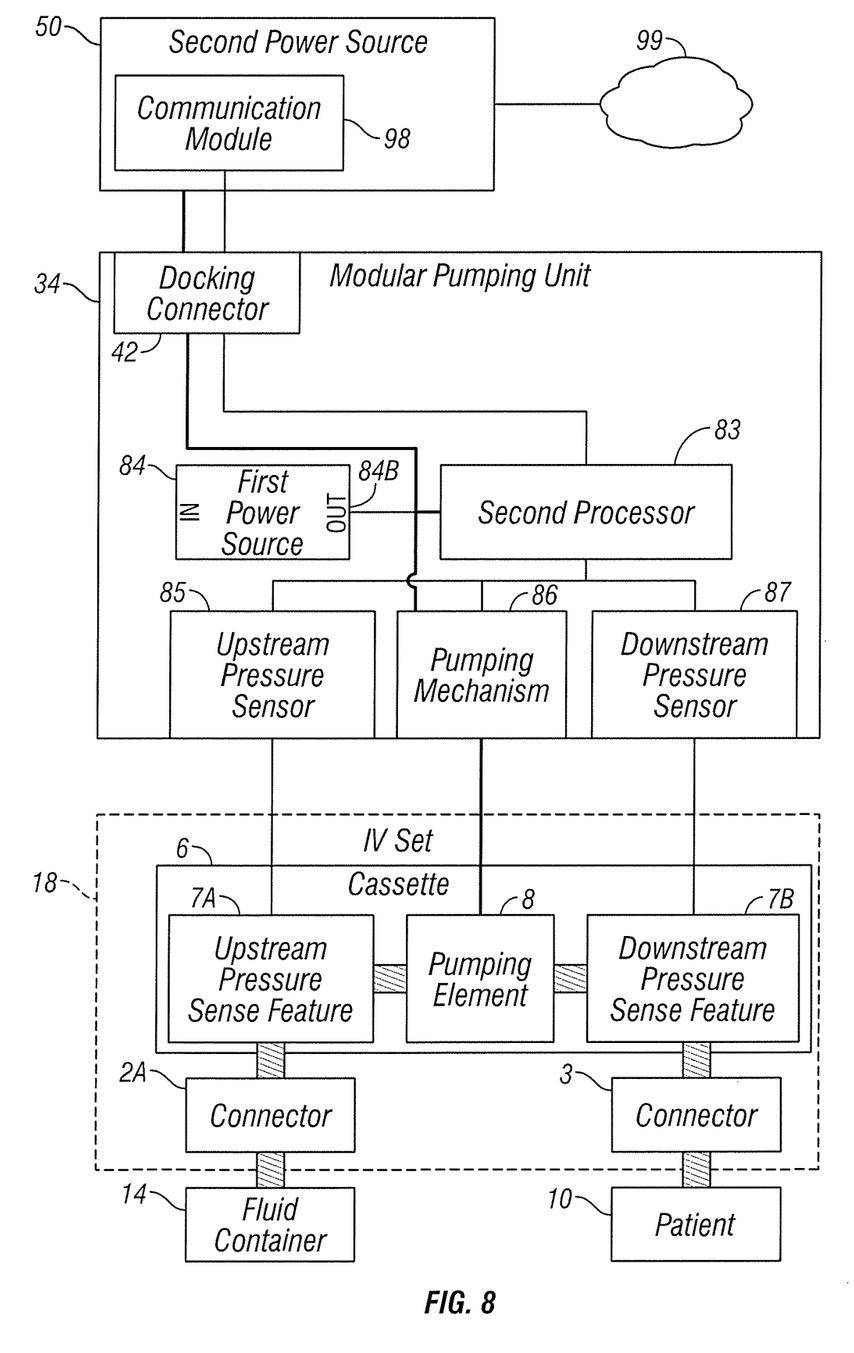
FIG. 8 is a block diagram of an alternate example configuration of a modular infusion system according to certain aspects of the present disclosure.

FIG. 8 is a block diagram of an alternate example configuration of a modular infusion system 30 according to certain aspects of the present disclosure. In this example configuration, the modular pumping unit 34 and the IV set 18 are identical to those shown in FIG. 7. FIG. 8 illustrates the configuration of modular infusion system 30 after the modular pumping unit 34 has been undocked from the primary control unit 32 (not shown) and a second power source 50 has been coupled to the modular pumping unit 34 through docking connector 42. The second power source 50 provides power, as indicated by the thicker connecting lines, through docking connector 42 to both the second processor 83 and the pumping mechanism 86, making modular pumping unit 34 capable of extended operation, compared to embodiments in which the pumping mechanism runs from the first power source 84, while undocked. In certain embodiments, the second power source 50 is coupled to the first power source 84 and recharges the first power source 84. Second power source 50 also includes, in this example, a communication module 98 that provides wireless communication capability to an external network shown as a "cloud" 99. In certain embodiments, the communication module 98 is a part of the modular pumping unit 34. In certain embodiments, cloud 99 is a cellular phone network, wherein communication module 98 connects through the cellular network to a hospital or other monitoring location and therein to a monitoring application running on a processor (not shown). In certain other embodiments, cloud 99 is a wireless Ethernet network within a hospital, and communication module 98 connects to the server through the Ethernet network. In certain other embodiments, cloud 99 is a short-range wireless network supported by one or more of Bluetooth, ZigBee, or a proprietary communication protocol. The communication link between second processor 83 through communication module 98 to a monitoring application allows operational data to be sent from the second processor 83 to the monitoring application and for the monitoring application to upload new settings and new firmware to the second processor 83. In certain embodiments, the monitoring application is running on a hospital server. In certain other embodiments, the monitoring application is running on the primary control unit 32. In certain other embodiments, the monitoring application is running on a portable device carried by an attending physician. In certain embodiments, the second processor 83 communicates with a monitoring application that functions as a gateway and distributes a portion of the information received from the second processor 83 to one or more secondary applications running on the same processor or other processors.

Figure 9:
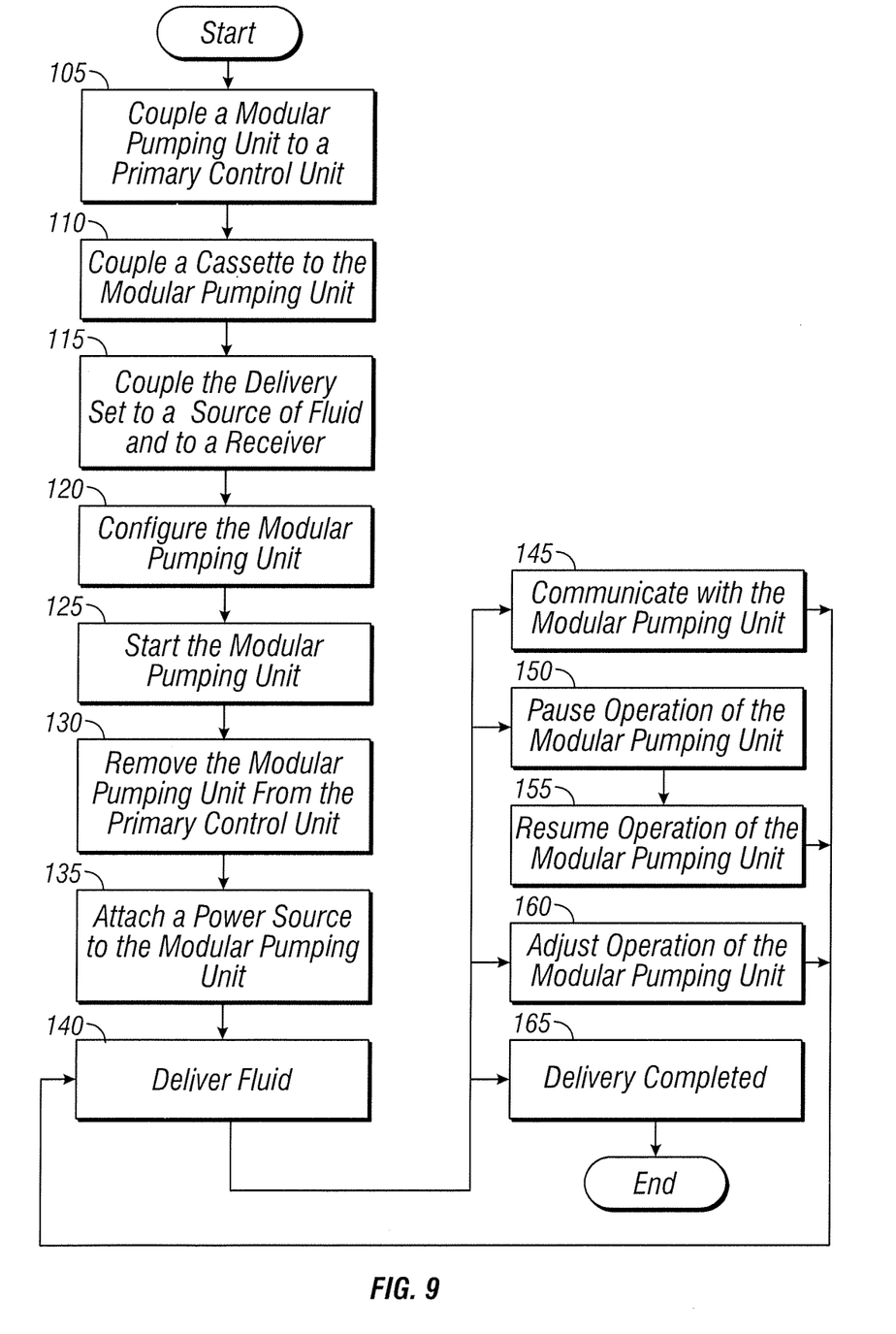
FIG. 9 is a flowchart of an example method of delivering fluid according to certain aspects of the present disclosure.

FIG. 9 is a flowchart of an exemplary method of delivering fluid according to certain aspects of the present disclosure. This method will be described with reference to an example of a nurse using the modular infusion system 30 of FIG. 4 and the IV set of FIG. 2 to administer a medical fluid to a patient 10 in a hospital. The method is equally applicable, however, to other settings and uses and to nonmedical applications. The process starts in step 105 wherein the nurse docks a modular pumping unit 34 to a primary control unit 32. In step 110, the nurse couples the cassette 6 of an IV set 18 to the modular pumping unit 34 and, in step 115, connects the bag spike 2 to a fluid container 14 and connects the needleless connector 3 to an infusion needle inserted in an arm of patient 10. The nurse configures the modular pumping unit 34 using the controls of the primary control unit 32 in step 120. In step 125, the nurse starts the modular pumping unit 34 using the controls of the primary control unit 32. In this example, the nurse then removes the modular pumping unit 34 from the primary control unit 32 in step 130 and, in step 135, attaches a power source such as a battery pack 50 to the modular pumping unit 34. Step 140 consists of continued operation of the modular pumping unit 34 in delivering fluid to the patient 10. The process will remain in step 140 until one of the steps 145, 150, 160, or 165 is initiated.

In this exemplary process, a nurse initiates step 145, wherein a communication link is established between the modular pumping unit 34 and the monitoring application. In certain embodiments, step 145 is initiated by the monitoring application. In certain embodiments, the second processor 83 initiates step 145. Once established, the second processor 83 downloads operational information regarding the modular pumping unit 34 to the monitoring application. In certain embodiments, the monitoring application uploads new operating parameters to the modular pumping unit 34. In certain other embodiments, the monitoring application uploads new firmware. After the data exchange is complete, the process reverts to step 140 wherein the modular pumping unit 34 continues to deliver medical fluid to the patient 10.

Step 150 is initiated by the nurse, in this example, when it is desirable to pause the operation of the modular pumping unit 34, such as during exchange of an empty fluid container 14 for a full fluid container 14. In certain embodiments, the patient 10 initiates step 150. When it is desired to resume operation of the modular pumping unit 34, the nurse initiates step 155 wherein the modular infusion pump 34 resumes operation and the process returns to step 140.

Step 160 is initiated by the nurse when it is desirable to change one or more of the operating parameters of the modular pumping unit 34 such as when an attending physician orders that the rate of administering the medical fluid be increased. In certain embodiments, the rate is changed through the wireless connection between the modular pumping unit 34 and the primary control unit 32 or other monitoring/control system. In certain embodiments, the patient 10 initiates step 160. To increase the flow rate, the nurse presses button 52A and verifies on display 54 that the new flow rate matches the rate ordered by the attending physician. Once the new operating parameters have been implemented, the processor reverts to step 140.

The last alternate action is step 165, wherein the delivery of the medical fluid in step 140 has been completed. In this example, the modular pumping unit 34 automatically detects the depletion of the fluid in fluid container 14 and moves from step 140 to step 160, stops the operation of the pumping mechanism 86 and displays a message such as "COMPLETE" on the display 54. As this administration of medical fluid is now over, the process moves to the end.

In certain embodiments, the modular pumping unit 34 is non-detachably coupled to a fluid container 14 in the pharmacy and then sent up to the patient 10. The process would start, in these embodiments, at step 110 wherein the modular pumping unit 34 is coupled to an IV set 18 and the IV set 18 is then coupled to a fluid container 14 that is part of step 115. The modular pumping unit 34 is then programmed in step 120 with information related to the medical fluid of the coupled fluid container 14. In certain embodiments, this information includes an identifier of the patient 10 for whom this medical fluid is intended. This unitized modular pumping unit/IV set/fluid container 34/18/14 is then delivered to the patient 10 whereupon the modular pumping unit 34 is coupled to the primary control unit 32 as shown in step 105. The caregiver may further program or configure the modular pumping unit 34, repeating a portion of step 120, and then proceed to step 125 and follow the sequence previously described from that point on.

It can be seen that the disclosed embodiments of the modular infusion system provide an easily reconfigured system. Individual modules can be added or removed from a primary control unit without having an effect on the operation of the other modules that are docked to that primary control unit, making unused modules available for use with other primary control units. The ability of the individual modular pumping units to continue to operate and deliver fluid to a patient provides increased mobility to the patient, making it easier for them to move around for activities such as going to the bathroom and walking in the hallway. The individual modular pumping units can be carried by patients when they are outside of the hospital, allowing them to continue to receive treatment by infusion while traveling between locations or during their normal activities.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A pump comprising:
    a primary control unit comprising a first processor that configures operation of one or more modular pumping units, and a plurality of docking stations configured to accept one or more modular pumping units such that each modular pumping unit may be docked and undocked in a docking station without docking or undocking another of the modular pumping units; and
    a plurality of modular pumping units removably docked to the primary control unit, each modular pumping unit comprising:
        a pumping mechanism;
        a second processor configured to (i) control the respective pumping mechanism according to one or more operating parameters and (ii) communicate with the first processor; and
        a first power source;
        wherein the pumping mechanism is configured to manipulate a portion of a fluid delivery set to pump a fluid;
    wherein the first processor is configured to communicate the one or more operating parameters to the second processor when the modular pumping unit is docked to the primary control unit; and
    a second power source removably coupled to the modular pumping unit when the modular pumping unit is undocked, the second power source comprising a communication module configured to communicate wirelessly with the first processor;
    wherein the second processor of each modular pumping unit is configured to operate according to the one or more operating parameters to pump the fluid after being undocked from the primary control unit, and modify the operation of the modular pumping unit in response to actuation of at least one input element on the modular pumping unit.

2. The pump of claim 1, wherein the modular pumping unit further comprises
    at least one visual indicator coupled to the second processor, wherein the second processor is configured to provide information through the at least one visual indicator about at least one aspect of the operation of the modular pumping unit.

3. The pump of claim 2, wherein the second processor is configured to perform at least one operation of the pumping mechanism of the set of start, stop, pause, and resume in response to actuation of the at least one input element.

4. The pump of claim 1, wherein the first power source is coupled to the second processor, wherein the first power source is configured to provide power to the second processor when the modular pumping unit is not docked to the primary control unit; and
    wherein the second power source is configured to provide power to the second processor and the pumping mechanism when the modular pumping unit is not docked to the primary control unit.

5. The pump of claim 4, wherein the modular pumping unit is further configured to provide power to the pumping mechanism from the first power source when the modular pumping unit is not docked to the primary control unit.

6. The pump of claim 4, wherein the primary control unit is configured to charge the first power source when the modular pumping unit is docked to the primary control unit.

7. The pump of claim 4, wherein the modular pumping unit is further configured to charge the first power source from the second power source when the modular pumping unit is not docked to the primary control unit.

8. The pump of claim 4, wherein the modular pumping unit further comprises a docking connector coupled to the second processor and pumping mechanism, the docking connector configured to couple to the primary control unit when the modular pumping unit is docked to the primary control unit, and wherein the second power source is configured to removably couple to the docking connector.

9. The pump of claim 4, wherein the communication module is configured to communicate with a monitoring application over a cellular phone network.

10. The pump of claim 4, wherein the communication module is configured to communicate with a monitoring application over an Ethernet network.

11. The pump of claim 4, wherein the communication module is configured to communicate with a monitoring application over a short-range wireless network.

12. The pump of claim 4, wherein the communication module is configured to receive programming instructions and provide them to the second processor.

13. The pump of claim 1, wherein:
the fluid comprises a medical fluid;
the fluid delivery set comprises a disposable intravenous (IV) set; and
the modular pumping unit is configured to pump IV fluids fluid to a patient.

14. The pump of claim 13, wherein:
the IV set comprises a cassette;
the cassette comprises a pumping element;
the pumping element comprises the portion of the IV set that is manipulated by the modular pumping unit;
the cassette is configured to couple to the modular pumping unit;
the IV set comprises an upstream end configured to couple to a source of medical fluid and a downstream end configured to couple to a patient infusion device;
the cassette further comprises at least one pressure sensing feature fluidically coupled to at least one of an upstream side and a downstream side of the pumping element;
the modular pumping unit further comprises at least one pressure sensor coupled to the second processor, the pressure sensor configured to measure the pressure of the fluid within the pressure sensing feature.

15. The pump of claim 14, wherein the pumping mechanism comprises at least one positive displacement pumping chamber configured to create a partial vacuum at the upstream end of the IV set sufficient to draw fluid from a non-vented syringe.

16. The pump of claim 1, wherein the one or more operating parameters are programmed into the second processor and the second processor transfers the one or more operating parameters to the first processor when the modular pumping unit is docked to the primary control unit.

17. A method of delivering fluid, the method comprising the steps of:
coupling a plurality of modular pumping units to a primary control unit comprising a plurality of docking stations configured to accept one or more modular pumping units such that each modular pumping unit may be docked and undocked in a docking station without docking or undocking another of the modular pumping units;
coupling a cassette of a delivery set to the modular pumping unit;
coupling the delivery set to a source of fluid and to a receiver, such that manipulation of the cassette will transfer fluid from the source to the receiver;
configuring one or more operating parameters into a first processor of the primary control unit;
configuring the modular pumping unit to manipulate the cassette, wherein the configuring is accomplished through transfer of the one or more operating parameters from the first processor to a second processor of each modular pumping unit coupled to the primary control unit;
modifying the operation of the modular pumping unit by the second processor in response to actuation of at least one input element on the modular pumping unit;
starting the modular pumping unit, wherein the starting is accomplished through the primary control unit;
removing the modular pumping unit from the primary control unit;
coupling a power source to the modular pumping unit, the power source comprising a communication module configured to communicate wirelessly with a monitoring application operating on the first processor; and
pumping the fluid from the source to the receiver.

18. The method of claim 17, wherein:
the delivery set comprises an IV set;
the fluid comprises a medical fluid; and
the receiver is a patient.

19. The method of claim 17, further comprising the step of communicating the one or more operating parameters wirelessly between the modular pumping unit and the monitoring application.

20. The method of claim 17, further comprising the steps of:
stopping the modular pumping unit using a control element that is a part of the modular pumping unit;
adjusting the flow rate using the control element that are a part of the modular pumping unit; and
starting the modular pumping unit using the control element that are a part of the modular pumping unit.

21. A modular pumping unit comprising:
a pumping mechanism configured to manipulate a portion of a fluid delivery set to pump a fluid;
a first processor configured to control the pumping mechanism; and
a first power source;
wherein the modular pumping unit is configured to removably dock with a primary control unit comprising a second processor and a plurality of docking stations configured to accept one or more modular pumping units such that each modular pumping unit may be docked and undocked in a docking station without docking or undocking another of the modular pumping units, the modular pumping unit further configured to pump the fluid while docked and undocked;
wherein (i) the first processor is coupled to the second processor when the modular pumping unit is docked such that the second processor transfers programming, including one or more operating parameters, to the first processor, and (ii) the first processor is configured to modify the operation of the modular pumping unit in response to actuation of at least one input element on the modular pumping unit; and
a second power source removably coupled to the modular pumping unit when the modular pumping unit is undocked, the second power source comprising a communication module configured to communicate wirelessly with the second processor.

22. The modular pumping unit of claim 21, wherein the first power source is configured to provide power to at least the first processor when the modular pumping unit is undocked from the primary control unit.

23. The modular pumping unit of claim 22, wherein the first power source is further configured to provide power to the pumping mechanism when the modular pumping unit is undocked from the primary control unit.

24. The modular pumping unit of claim 22, wherein the modular pumping unit is configured to draw power from the second power source while undocked from the primary control unit.

25. The modular pumping unit of claim 24, wherein the modular pumping unit is further configured to charge the first power source from the second power source when the modular pumping unit is not docked to the primary control unit.

26. The modular pumping unit of claim 24, further comprising a docking connector coupled to the first processor and the pumping mechanism, the docking connector configured to couple to the primary control unit when the modular pumping unit is docked to the primary control unit, the docking connector further configured to removably couple to the second power source.

27. The modular pumping unit of claim 21, further comprising:
  at least one visual indicator coupled to the first processor, wherein the first processor is configured to provide information through the at least one visual indicator about at least one aspect of the operation of the modular pumping unit; and
  at least one input element coupled to the first processor, wherein the first processor is configured to modify the operation of the modular pumping unit in response to actuation of the at least one input element.

28. The modular pumping unit of claim 21, wherein:
the fluid comprises a medical fluid;
the fluid delivery set comprises a disposable IV set; and
the modular pumping unit is configured to pump IV fluid to a patient.

29. The modular pumping unit of claim 28, wherein:
the IV set comprises a cassette;
the cassette comprises a pumping element;
the pumping element comprises the portion of the IV set that is manipulated by the modular pumping unit;
the cassette is configured to couple to the modular pumping unit;
the IV set comprises an upstream end configured to couple to a source of medical fluid and a downstream end configured to couple to a patient infusion device;
the cassette further comprises at least one pressure sensing feature fluidically coupled to at least one of the upstream side and the downstream side of the pumping element;
the modular pumping unit further comprises at least one pressure sensor coupled to the first processor, the pressure sensor configured to measure the pressure of the fluid within the pressure sensing feature.

* * * * *